US012558251B2

(12) United States Patent
Windeballe et al.

(10) Patent No.: US 12,558,251 B2
(45) Date of Patent: Feb. 24, 2026

(54) BASE PLATE FOR AN OSTOMY APPLIANCE

(71) Applicant: Coloplast A/S, Humlebaek (DK)

(72) Inventors: Lars Stendevad Windeballe, Virum (DK); Stephanie Knoedler, Nivaa (DK); Lars F. Molzen, Alleroed (DK); Jais Ask Hansen, Jaegerspris (DK); Kamilla Grove Sund, Alleroed (DK); Jose Manuel Roman-Marin, Copenhagen N (DK); Jesper Kenneth Olsen, Birkeroed (DK); Jonas Emborg, Frederikssund (DK)

(73) Assignee: Coloplast A/S, Humlebaek (DK)

( * ) Notice: Subject to any disclaimer, the term of this patent is extended or adjusted under 35 U.S.C. 154(b) by 636 days.

(21) Appl. No.: 17/792,742

(22) PCT Filed: Jan. 20, 2021

(86) PCT No.: PCT/DK2021/050018
§ 371 (c)(1),
(2) Date: Jul. 14, 2022

(87) PCT Pub. No.: WO2021/148097
PCT Pub. Date: Jul. 29, 2021

(65) Prior Publication Data
US 2023/0031979 A1      Feb. 2, 2023

(30) Foreign Application Priority Data
Jan. 20, 2020    (DK) ........................... PA 2020 70039

(51) Int. Cl.
*A61F 5/44*       (2006.01)
*A61F 5/443*      (2006.01)
*A61F 5/445*      (2006.01)

(52) U.S. Cl.
CPC ............ *A61F 5/4404* (2013.01); *A61F 5/443* (2013.01); *A61F 5/445* (2013.01)

(58) Field of Classification Search
CPC .. A61F 13/42; A61F 2005/4486; A61F 5/445; A61F 13/00055; A61F 13/15577; A61F 5/4404; A61F 5/443
See application file for complete search history.

(56) References Cited

U.S. PATENT DOCUMENTS 6,171,289 B1      1/2001  Millot et al.
2019/0133810 A1*  5/2019  Seres ..................... A61B 5/445
(Continued)

FOREIGN PATENT DOCUMENTS

WO      WO-9508440 A1 *  3/1995  ............. A61F 5/445
WO      2007098762 A1    9/2007
(Continued)

*Primary Examiner* — Philip R Wiest
*Assistant Examiner* — Eric Rassavong
(74) *Attorney, Agent, or Firm* — Coloplast Corp., Coloplast A/S; Nick Baumann

(57)      ABSTRACT

A base plate (10) for an ostomy appliance is disclosed. The base plate has a proximal surface and a distal surface. The base plate comprises a first adhesive layer (110) having a proximal side including a proximal surface (111) and a distal side including a distal surface (112), an electrode assembly (120) comprising one or more electrodes (120'), and a top film (100) having a proximal surface and a distal surface. The top film is arranged on the distal side of the first adhesive layer. The electrode assembly is arranged on the proximal surface of the top film. The distal surface of the top film is the distal surface of the base plate.

21 Claims, 5 Drawing Sheets

(56)                    References Cited

U.S. PATENT DOCUMENTS

2020/0000624 A1      1/2020  Gibbons et al.
2020/0246177 A1*     8/2020  Hansen .................. A61F 5/445

FOREIGN PATENT DOCUMENTS

WO          2015014774  A1      2/2015
WO          2019120438  A1      6/2019
WO          2019120450  A1      6/2019
WO          2019233807  A1     12/2019

* cited by examiner

BASE PLATE FOR AN OSTOMY APPLIANCE

The present disclosure relates to a base plate for an ostomy appliance, the base plate comprising an adhesive layer, a top film, and an electrode assembly; and to a method of manufacturing such a base plate. In particular, the present disclosure relates to a base plate having sensing means and improved flexible and elastic properties.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
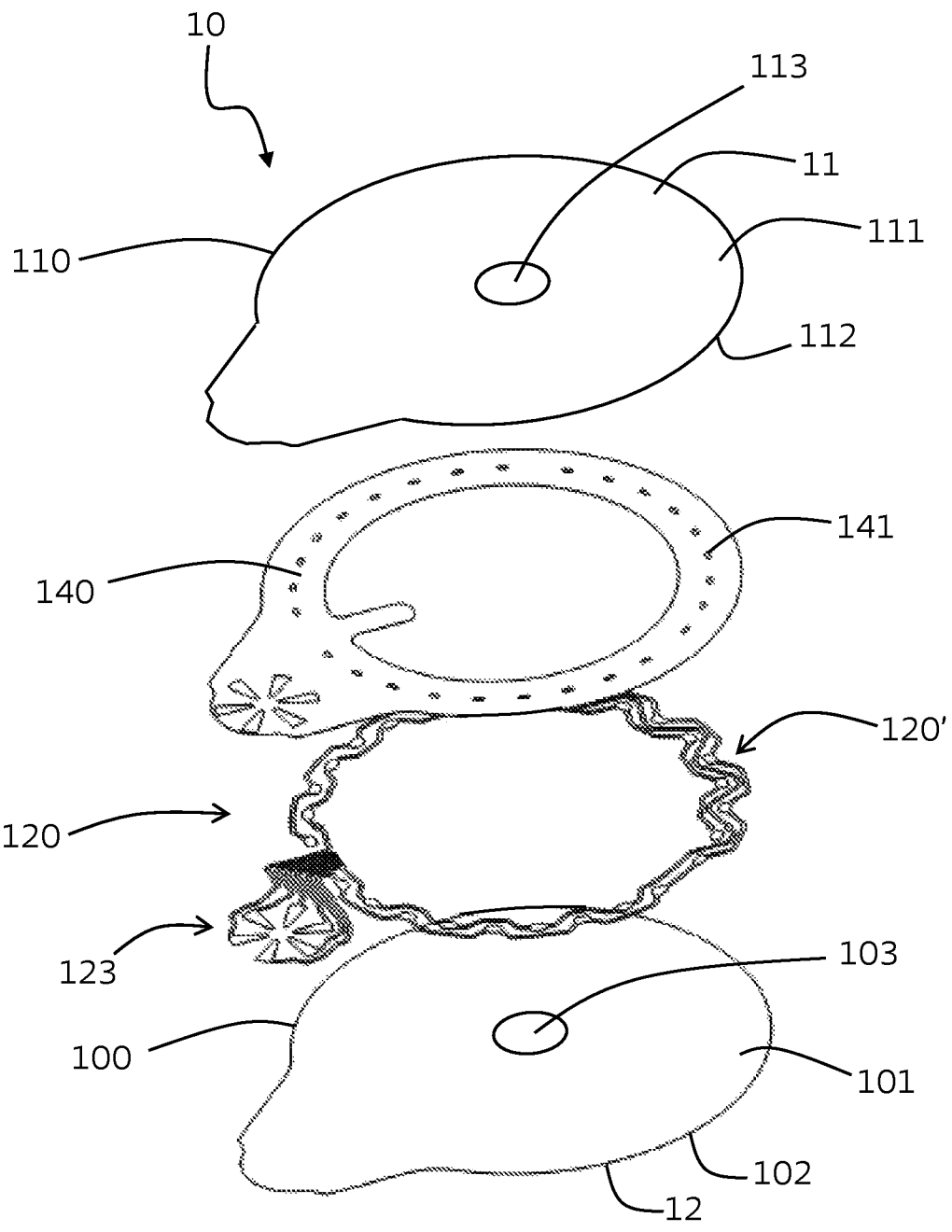
FIG. 1 illustrates an exploded view of a base plate according to an embodiment of the invention.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g., "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The present disclosure provides a base plate comprising an adhesive, an electrode assembly, and a top film, and a method for manufacturing such as base plate.

In a first aspect of the invention, a base plate for an ostomy appliance is disclosed. The base plate has a proximal surface and a distal surface. The base plate comprises a first adhesive layer having a proximal side including a proximal surface and a distal side including a distal surface, an electrode assembly comprising one or more electrodes, and a top film having a proximal surface and a distal surface. The top film is arranged on the distal side of the first adhesive layer. The electrode assembly is arranged on the proximal surface of the top film. The distal surface of the top film is the distal surface of the base plate.

Through the provision of an electrode assembly, the base plate provides sensing means (sensors), such as means for detecting the adhesive performance of the first adhesive layer and/or the presence of stomal output propagating in the interface between the first adhesive layer and a skin surface of a user wearing the base plate. According to the first aspect of the invention, the sensors are provided through the provision of an electrode assembly, the electrode assembly comprising one or more electrodes forming sensors. A monitor device can be couplable to the one or more electrodes of the electrode assembly, whereby the monitor device can monitor changes in certain electrical quantities, e.g., resistance, conductance, or capacitance, to determine the state or "health" (e.g., adhesive performance or the presence of a propagating leak in the interface between the skin and the base plate) of the base plate. The base plate is configured for attachment to the skin surface, such as the peristomal skin surface, of a user by means of the first adhesive layer. In embodiments, the base plate further comprises an ostomy bag for collecting output from the stoma.

Also disclosed is an ostomy system and devices thereof, such as an ostomy appliance, a base plate for an ostomy appliance, a sensor patch for application to a base plate, a monitor device, and optionally one or more accessory devices. Further, methods related to the ostomy system and devices thereof are disclosed. An accessory device (also referred to as an external device) can be a mobile phone or other handheld device. In embodiments, an accessory device is a personal electronic device, e.g., a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

Also disclosed is an ostomy system and devices thereof, such as an ostomy appliance, a base plate for an ostomy appliance, a sensor patch for application to a base plate, a monitor device, and optionally one or more accessory devices which either alone or together facilitate reliable determination of the nature, severity, and rapidness of moisture propagation in the adhesive material provided for attaching the base plate and/or sensor patch to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage. Determination of moisture pattern types or angular leakage patterns is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e., the base plate and the ostomy pouch are releasably coupled e.g., with a mechanical and/or an adhesive coupling, e.g., to allow that a plurality of ostomy pouches can be utilized (exchanged) with one base plate. Further, a two-part ostomy appliance can facilitate correct application of the base plate to skin, e.g., to an improved user sight of the stomal region. In embodiments, the ostomy appliance is a one-part ostomy appliance, i.e., the base plate and the ostomy pouch are fixedly attached to each other. The base plate is configured for coupling to a user's stoma and/or skin surrounding the stoma, such as a peristomal skin area.

In embodiments, the ostomy appliance includes a base plate, such as a monolithic, one-piece base plate, e.g., integrated with a sensor assembly part, or a separate sensor assembly part, such as a sensor assembly part to be subsequently applied to a base plate. In other examples, the sensor assembly part is a sensor patch for application to the base plate, such as the proximal surface of the base plate. Thereby, an arbitrary base plate, such as a conventional/generic base plate, can achieve the features as described herein.

Features as described with respect to sensing/monitoring capabilities of the base plate herein can be provided by a sensor assembly of a sensor patch to be applied to a base plate, e.g., by the user, and vice versa. In embodiments, the sensor patch is adapted to adhere to a generic base plate. Thus, in embodiments, the features disclosed herein may as well be provided in a sensor patch to be adhered to a proximal surface of a generic base. In embodiments, a method of attaching a base plate having sensing capabilities, e.g., through the provision of a sensor patch, to a user's stoma and/or skin surrounding the stoma, such as the peristomal skin area, comprises attaching the sensor patch to a base plate and attaching the base plate, i.e., together with the attached sensor patch, to the user's stoma and/or skin surrounding the stoma, such as the peristomal skin area.

Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e., on a distal surface of the sensor patch.

In embodiments, the first adhesive layer is made of a first composition. The first composition can comprise one or more polyisobutenes and/or styrene-isoprene-styrene. The first composition can comprise one or more hydrocolloids. The first composition can comprise one or more water soluble or water swellable hydrocolloids. The first composition can be a pressure sensitive adhesive composition suitable for medical purposes comprising a rubbery elastomeric base and one or more water soluble or water swellable hydrocolloids. The first composition can comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer can for example be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semi-synthetic hydrocolloids and synthetic hydrocolloids. In embodiments, the first composition can comprise 20-60% hydrocolloids. A preferred hydrocolloid is carboxymethylcellulose (CMC). The first composition can optionally contain other components, such as fillers, tackifiers, plasticizers, and other additives.

The first adhesive layer can have a substantially uniform thickness. The first adhesive layer can have a thickness in the range from 0.1 mm to 1.5 mm, e.g., in the range from 0.2 mm to 1.2 mm, such as 0.8 mm or 1.0 mm. The first adhesive layer can have a primary thickness in a primary part of the first adhesive layer, e.g., in a primary region within a primary radial distance or in a primary radial distance range from a centre point of a stomal opening provided in the base plate. The primary thickness can be in the range from 0.2 mm to 1.5 mm, such as about 1.0 mm. The primary radial distance can be in the range from 20 mm to 50 mm, such as in the range from 25 mm to 35 mm, e.g., 30 mm. The first adhesive layer can have a secondary thickness in a secondary part of the first adhesive layer, e.g., in a secondary region outside a secondary radial distance or in a secondary radial distance range from the centre point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g., 30 mm.

In embodiments, the base plate comprises a second layer. In embodiments, the second layer is an adhesive layer. In embodiments, the second layer is arranged on a distal side of the first adhesive layer. In embodiments, the second layer comprises a proximal surface and a distal surface. In embodiments, the proximal surface is adhered or in contact with the distal surface of the first adhesive layer. In embodiments, the second layer has a second radial extension that is larger than a first radial extension of the first adhesive layer at least in a first angular range of the base plate. Accordingly, a part of a proximal surface of the second layer can be configured for attachment to the skin surface of a user. The part of a proximal surface of the second layer configured for attachment to the skin surface of a user is also denoted the skin attachment surface of the second adhesive layer. The second layer can have a stomal opening, such as a second layer stomal opening and/or a second adhesive stomal opening, with a centre point.

In embodiments, the second adhesive layer is made of a second composition. In embodiments, the second composition comprises one or more polyisobutenes and/or styrene-isoprene-styrene. In embodiments, the second composition comprises one or more hydrocolloids. In embodiments, the second composition comprises one or more water soluble or water swellable hydrocolloids. In embodiments, the second composition is a pressure sensitive adhesive composition suitable for medical purposes comprising a rubbery elastomeric base and one or more water soluble or water swellable hydrocolloids. In embodiments, the second composition comprises one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition can comprise 20-60% hydrocolloids. A preferred hydrocolloid is carboxymethyl cellulose (CMC). Optionally, the second composition can contain other components, such as fillers, tackifiers, plasticizers, and/or other additives.

Different ratio of contents can change properties of the first and/or second adhesive layers. In embodiments, the second adhesive layer and the first adhesive layer have different properties. In embodiments, the second adhesive layer (second composition) and the first adhesive layer (first composition) have different ratios of polyisobutenes, styrene-isoprene-styrene, and/or hydrocolloids. For example, the second adhesive layer can provide a stronger attachment to the skin compared to attachment to the skin provided by the first adhesive layer. Alternatively, or additionally, the second adhesive layer can be thinner than the first adhesive layer. Alternatively, or additionally, the second adhesive layer can be less water and/or sweat absorbing than the first adhesive layer. Alternatively, or additionally, the second adhesive layer can be less moldable than the first adhesive layer. In embodiments, the second adhesive layer provides a second barrier against leakage.

The second layer can have a substantially uniform thickness. The second layer can have a thickness in the range from 0.1 mm to 1.5 mm, e.g., in the range from 0.2 mm to 1.0 mm, such as 0.5 mm, 0.6 mm, or 0.7 mm.

Providing a base plate having sensing capabilities, e.g., through an incorporated sensor assembly or through a sensor patch comprising a sensor assembly, provides for an optimum or improved use of an ostomy appliance. In particular, it is facilitated that a base plate is not changed too late (leading to adhesive failure, leakage, and/or skin damage), or at least that a user is informed that a leakage will happen, is happening, or has happened. Accordingly, the user or a health care professional is able to monitor and plan the use of the ostomy appliance.

In embodiments, the electrode assembly of the base plate comprises one or more electrodes, such as a plurality of electrodes, such as two, three, four, five, six, seven or more electrodes. According to the first aspect of the invention, the electrode assembly of the base plate, and hence the one or more electrodes, is arranged, e.g., formed, e.g., printed, on the proximal surface of the top film. In embodiments, the electrode assembly and the top film in combination forms a sensor assembly of the base plate. In embodiments, one or more, such as two or more, electrodes of the electrode assembly forms one or more sensors configured to detect changes in resistance, conductance, and/or capacitance of the first adhesive layer and/or to detect a short-circuit, e.g., a short-circuit caused by a liquid path between two or more electrodes of the electrode assembly.

In embodiments, an electrode of the electrode assembly of the base plate comprises a connection part for connecting the electrode(s) to other components and/or interface terminals/terminal elements, such as for connecting the electrodes to a monitor device. In embodiments, an electrode comprises one or more conductor parts and/or one or more sensing parts. A conductor part can be considered part of an electrode connecting two or more sensing parts, and/or connecting a sensing part with a connection part of the respective electrode. A sensing part can be considered a part of the electrode being suitable for sensing, e.g., liquid, such as liquid content, and/or output, such as output resulting from a leakage, or an imminent leakage. The sensing part can be suitable for sensing e.g., by its shape, said shape potentially being circular, oval, or rectangular. Thus, the conductor part can conduct a signal arising from the sensing part. In embodiments, an electrode comprises alternating conductor parts and sensing parts. The electrode assembly can comprise a first electrode, a second electrode, and optionally a third electrode. The electrode assembly can comprise a fourth electrode and/or a fifth electrode. The electrode assembly optionally comprises a sixth electrode. In embodiments, the electrode assembly comprises a ground electrode. The ground electrode can comprise a first electrode part. In embodiments, the first electrode part of the ground electrode forms a ground or reference for the first electrode. In embodiments, the first electrode part forms a closed loop. The ground electrode can comprise a second electrode part.

In embodiments, the second electrode part of the ground electrode forms a ground or reference for the second electrode. The ground electrode can comprise a third electrode part. In embodiments, the third electrode part of the ground electrode forms a ground or reference for the third electrode. The ground electrode can comprise a fourth electrode part. In embodiments, the fourth electrode part of the ground electrode forms a ground or reference for the fourth electrode and/or the fifth electrode. In embodiments, the ground electrode is configured as or forms a (common) reference electrode for some or all of the other electrodes of the electrode assembly.

In embodiments, the first adhesive layer comprises a plurality of sensor point openings. In embodiments, a sensor point opening of the first adhesive layer is configured to overlap a (sensing) part of an electrode of the electrode assembly, e.g., to form a sensor point. In embodiments, the sensor point openings extend entirely through the first adhesive layer, such as to expose at least parts of the electrode assembly to the surroundings, such as to provide means for establishing a short-circuit between a first and a second electrode, a short-circuit being indicative of a presence of liquid, such as output, on the proximal surface of the base plate. Thus, in embodiments, the sensor point openings provide means for detecting the presence of liquid on the proximal surface of the base plate by monitoring the voltage across two electrodes of the electrode assembly. The presence of liquid on the proximal surface of the base plate may be indicative of output propagating in the interface between the proximal surface of the base plate and the peristomal skin surface of a user. In embodiments, the first adhesive layer comprises at least 10 sensor point openings, such as between 20 and 50 sensor point openings, in order to provide adequate leakage detection around the stoma of the user. In embodiments, the sensor point openings have a diameter of at least 1 mm, such as between 1.0 mm and 4.0 mm.

The one or more electrodes of the electrode assembly are electrically conductive and can comprise one or more of metallic (e.g., silver, copper, gold, titanium, aluminum, stainless steel or other), ceramic (e.g., ITO or other), polymeric (e.g., PEDOT, PANI, PPy or other), and carbonaceous (e.g., carbon black, carbon nanotube, carbon fiber, graphene, graphite, or other) materials. In embodiments, the electrodes can be wire electrodes or one-dimensional electrodes resembling a string or wire. In embodiments, the electrodes can have a width and/or thickness being considerably smaller than their length. In embodiments, the width and/or thickness of the electrodes can be up to 50 times smaller than the length of the electrodes. In embodiments, the electrodes can be less than 3 mm wide, and more than 100 mm long. In a preferred embodiment, the electrodes of the electrode assembly are printed on the top film, whereby the electrode assembly comprises, such as consists of, conductive traces of a conductive ink, e.g., silver ink or carbon ink suitable for printing on a surface. Thus, in embodiments the electrode assembly comprises, such as consists of, a (hardened/cured) conductive ink. In embodiments, conductive ink is created by infusing graphite, silver, or other conductive materials, into ink.

In embodiments, by a top film, and film in general, is meant a coherent flexible and/or elastic sheet substantially covering the entire surface or side of an object, such as the first adhesive layer. The top film of the base plate serves at least two purposes; it provides a protection for the first adhesive layer and it provides a substrate for the electrode assembly. Thus, the top film may be denoted a protective top film. In particular, the top film protects the first adhesive layer from dirt and from external stress and strain, such as caused by handling. Further, the top film provides a certain rigidity/stiffness to the first adhesive layer, thereby easing handling, e.g., when applying the base plate to the skin surface. The top film may also be denoted a backing layer in the field. In embodiments, the distal and/or proximal surface of the top film is non-adhesive. In embodiments, the distal and/or proximal surface of the top film is adhesive.

In embodiments, the top film is flexible and/or elastic. In a preferred embodiment, the top film is flexible and elastic. In an embodiment, the top film is made of a polymeric material. In a preferred embodiment, the top film is made of polyurethane (PU), e.g., thermoplastic polyurethane (TPU).

In alternative embodiments, the top film material can be made of or comprise one or more of PTFE, PVDF, polyester (e.g., PET), a thermoplastic elastomer (TPE), polyimide, polyimide, Ethylene-vinyl acetate (EVA), polyurea, and/or silicones. Exemplary thermoplastic elastomers (TPEs) of the top film include styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

A (T)PU-film may be a preferred material for the top film due to its highly flexible and elastic properties allowing for a likewise flexible and elastic base plate. Further, (T)PU belongs to a group of materials being a suitable substrate for printed electrodes, i.e., (T)PU is a suitable substrate for an electrode printing process, whereby printed electrodes (conductive traces) can be formed on a surface of the (T)PU film.

In embodiments, the top film has a thickness between 20 μm and 60 μm, in particular between 35 μm and 50 μm, such as 42 μm. A thickness within the indicated range, such as 42 μm, has been found to be suitable for a base plate of an ostomy appliance, in particular because the indicated thickness provides an adequate amount of rigidity to the base plate, thereby easing handling, but reducing skin damage.

In examples where the first adhesive layer, the electrode assembly, and the top film are provided in a sensor patch for attachment to a base plate, the top film may be thinner, such as between 20 μm and 50 μm, in particular between 25 μm and 35 μm, such as 30 μm. A thickness within the indicated range of 25 μm to 35 μm, in particular of 30 μm, has been found to be suitable for a sensor patch for attachment to a base plate of an ostomy appliance. Since the thickness of the top film affects at least the flexibility of the product (e.g., the sensor patch or the base plate), one has to carefully select a thickness being suitable for the intended use, such that the product (sensor patch or base plate) is neither too stiff when adhered to the skin surface of the user (thereby causing increased risk of leakage or skin irritation) nor too flexible when handling (thereby reducing manageability). In the case of a sensor patch for attachment to a base plate for an ostomy appliance, it is envisioned that a particularly rigid sensor patch is less important, as the combined rigidity of the sensor patch when adhered to a base plate provides the user with adequate rigidity during application to the skin surface of the base plate with a sensor patch. Rather, providing the sensor patch with a relatively thinner top film provides a more flexible and elastic product allowing the user to manipulate the sensor patch easier, such that the sensor patch can be stretched and manipulated to fit according to desired needs on the proximal adhesive surface of the base plate prior to application to the skin surface. Further, a thinner top film (relative to a thickness of a top film of a generic base plate) of the sensor patch provides for a less rigid appliance when adhered to a generic base plate (where the thickness of the top film of the sensor patch and the thickness of the top film of the base plate both contribute to the rigidity of the combined appliance).

According to the first aspect of the invention, the top film of the base plate has a proximal surface and a distal surface. The top film is arranged on the distal side of the first adhesive layer, such as on the distal surface of the first adhesive layer. In other words, the proximal surface of the top film may face the distal surface of the first adhesive layer. When referring to the situation of the proximal surface of the top film being arranged on the distal surface of the first adhesive layer, it is understood that the electrode assembly is arranged on the proximal surface of the top film, and as such becomes sandwiched between the top film and the first adhesive layer. Thus, in embodiments, the electrode assembly, such as the one or more electrodes of the electrode assembly, has a distal surface arranged on the proximal surface of the top film and a proximal surface arranged on/facing towards the distal surface of the first adhesive layer. However, due to a negligible extent/coverage of the electrodes of the electrode assembly on the proximal surface of the top film, references to the distal/proximal surfaces of the electrodes are omitted to keep the discussion simple.

According to the first aspect of the invention, the electrode assembly of the base plate is arranged on the proximal surface of the top film. Thereby, the electrodes of the electrode assembly face towards the distal surface of the first adhesive layer. In embodiments, at least parts of the electrodes of the electrode assembly are in direct contact with the distal surface of the first adhesive layer and thus in direct contact with the first adhesive layer as such. In embodiments, by the electrode assembly being arranged on the proximal surface of the top film is meant that the electrodes of the electrode assembly are formed, such as printed, on the proximal surface of the top film. Thus, the electrodes of the electrode assembly are in direct contact with the proximal surface of the top film. Thereby, the top film may be considered a substrate or a support for the electrode assembly.

According to the first aspect of the invention, the distal surface of the top film is the distal surface of the base plate. In other words, the distal surface of the top film forms the distal surface of the base plate as such. Thus, the proximal surface of the top film is provided with the electrode assembly and the distal surface of the top film is the distal surface of the entire base plate of which the top film forms part of. Thereby, the top film doubles as a support for the one or more electrodes of the electrode assembly and as a protective film for the entire distal side of the base plate.

Thereby, it is facilitated that the base plate comprises only one coherent film, according to previous definitions, on the distal side of the first adhesive layer. Providing only one film on the distal side of the first adhesive layer of the base plate allows for a thin, flexible, and elastic base plate. Further, the cost associated with the base plate can be reduced as opposed to providing an intermediate film, such as an intermediate support film supporting the electrode assembly, arranged between the proximal surface of the top film and the distal surface of the first adhesive layer. Further, the consequently reduced complexity of the base plate provides for a reduced complexity of the production of such a base plate.

In embodiments, the base plate consists of a first adhesive layer, an electrode assembly, and a top film. In embodiments, the electrode assembly comprises an interface, such as an interface allowing electrical and/or mechanical connection to a monitor device. In embodiments, the base plate is further provided with a release liner arranged on the proximal surface of the first adhesive layer. The release liner is configured to be detached/peeled off the base plate prior to adhering the base plate to the skin surface of a user. Thus, the release liner is a protective barrier not forming part of the base plate in use, i.e., not forming part of the base plate when the proximal surface of the first adhesive layer is adhered to the skin surface of a user.

In an embodiment, the top film is the only polymeric layer of the base plate. In embodiments, the top film is the only flexible and elastic film material arranged on the distal side of the first adhesive layer. Thus, in embodiments, the base plate comprises one, and only one, polymeric film material on the distal side of the first adhesive layer. Thereby, as discussed above, is provided that the base plate is thin and flexible, and associated costs are reduced.

In an embodiment, the one or more electrodes of the electrode assembly are conductive traces, such as conductive traces printed on the proximal surface of the top film. By a conductive trace is meant an electrically conductive path created by a printing process wherein conductive ink, e.g., silver, is deposited on a substrate, e.g., the proximal surface of the top film according to an embodiment of the invention, according to a predefined pattern depending on the desired capabilities and properties of the electrode assembly. In embodiments, the electrode assembly consists of one or more conductive traces, such as of a plurality of conductive traces, and a monitor interface allowing for a connection to a monitor device.

In an embodiment, at least parts of the electrode assembly are in contact with the distal surface of the first adhesive layer. In embodiments, the entire electrode assembly is in contact with a distal surface of the first adhesive layer and/or entirely in contact with the proximal surface of the top film. According to the first aspect of the invention, the distal surface of the top film is the distal surface of the base plate. Consequently, by arranging the electrode assembly such that at least parts of said electrode assembly is in contact with the distal surface of the first adhesive layer and in contact with the proximal surface of the top film, there is no room for any additional film/sheet material covering the entire distal side/surface of the first adhesive layer. Thereby, the only film covering the entire distal side, according to previous definitions, is the top film. Thereby, the base plate comprises one, and only one, coherent film, such as one, and only one, polymeric film, covering the entire distal side of the first adhesive layer. In embodiments, at least parts of the electrode assembly, such as at least parts of the one or more electrodes, are masked from the first adhesive layer by means of a masking layer, also denoted a reinforcement layer in later discussions. The masking layer can be arranged according to a predefined pattern, thereby exposing certain parts of the electrode assembly to the distal surface of the first adhesive layer. Thus, the masking layer does not cover the entire distal side/surface of the first adhesive layer, and as such is not considered a film material according to previous definitions. In embodiments, the masking layer comprises sensor point openings corresponding to/aligned with sensor point openings of the first adhesive layer, such as to expose the electrodes to the surroundings through the first adhesive layer.

In an embodiment, the proximal surface of the top film is in contact with the distal surface of the first adhesive layer. Thus, in embodiments, the top film, including the electrode assembly arranged on the proximal surface thereof, is arranged on the distal surface of the first adhesive layer. Thereby, in line with the above discussion, there is no room for any additional film/sheet material covering the entire distal side/surface of the first adhesive layer.

In an embodiment, the base plate further comprises a flexible reinforcement layer arranged on the distal side of the first adhesive layer. In an embodiment, the flexible reinforcement layer (e.g., the masking layer introduced above) is bonded to the top film, such as to a surface of the top film, such as to the proximal and/or distal surface of the top film. By being bonded is meant that in regions of the bond, the reinforcement layer and the top film move/stretch together when stretched. Thus, the bond provides that the reinforcement layer can carry a load (stretch) applied to the base plate, thereby alleviating the effect (e.g., a break or plastic deformation) the load can cause the top film and/or electrodes provided thereupon.

In general, depending on the properties of the top film and/or first adhesive layer, the elasticity of the top film and/or first adhesive layer can exceed the elasticity of the one or more electrodes (conductive traces) of the electrode assembly. In other words, the one or more electrodes, especially when printed, can be less elastic than the top film and/or the first adhesive layer. Thereby, the risk of overstretching and thus rupturing the electrodes arises during handling of the base plate. However, by providing a flexible reinforcement layer in the base plate, such as bonded to a surface of the top film, the elasticity of the top film and/or first adhesive layer can be reduced to a point where overstretching of the electrodes is inhibited, or where the risk is greatly reduced. Thus, in embodiments, the elasticity of the reinforcement layer is less than the elasticity of the one or more electrodes of the electrode assembly, and/or the elasticity of the top film, and/or the elasticity of the first adhesive layer. Thereby, the reinforcement layer becomes a limiting component of the base plate in terms of elasticity, thereby reducing the overall elasticity in at least regions of the base plate, such that the electrodes of the base plate cannot be overstretched and thus rupture. In other words, in an embodiment, the reinforcement layer is configured to inhibit overstretching of the one or more electrodes of the electrode assembly. Further, the provision of a reinforcement layer may protect the base plate, such as the first adhesive layer, from tearing, such as in an edge portion of the base plate. Thus, in embodiments, a reinforcement layer is provided in an edge portion of the base plate, such as in particularly exposed regions of the edge. Thus, in embodiments, the reinforcement layer is arranged according to a predefined pattern. In embodiments, the predefined pattern is designed to inhibit overstretching of the one or more electrodes and/or to electrically insulate/mask at least parts of the one or more electrodes from the first adhesive layer and/or to reinforcement an edge portion of the base plate.

By elasticity is meant a material's ability to return to its original shape after a load, such as a uniaxial load, is removed (also known as elastic deformation). By having a high elasticity is meant that a material is capable of being stretched to a large extend before breaking and/or experiencing plastic deformation compared to a material having a low elasticity. In embodiments, the elasticity can be expressed in terms of Young's modulus E, generally expressed by:

$$E = \frac{\sigma(\varepsilon)}{\varepsilon} = \frac{FL_0}{A\Delta L},$$

where $\sigma(\varepsilon)$ is the tensile stress and $\varepsilon$ is the engineering extensional strain in the elastic portion of the physical stress-strain curve, and where F is the force exerted on an object under tension, $L_0$ is the original length of the object, A is the actual cross-sectional area, which equals the area of the cross-section perpendicular to the applied force, and $\Delta L$ is the amount by which the length of the object changes.

In embodiments, the base plate consists of a first adhesive layer, an electrode assembly, a reinforcement layer, and a top film. Optionally, the base plate further comprises a release liner.

In an embodiment, the reinforcement layer has a Young's modulus being greater than the Young's modulus of the top film and/or the one or more electrodes of the electrode assembly and/or the first adhesive layer. Thereby is provided that a greater force is required to stretch and deform and/or break the reinforcement layer than the top film and/or the one or more electrodes provided thereupon. Thereby, the reinforcement layer can withstand greater forces and thereby delimit the stretching of the top film and consequently the electrode assembly provided thereupon. Thus, the reinforcement layer is configured to carry a load applied to the base plate, rather than the electrodes, the top film, or the first adhesive layer doing so.

In embodiments, the reinforcement layer has an ultimate tensile strength being greater than an ultimate tensile strength of the top film and/or the one or more electrodes of the electrode assembly. By ultimate tensile strength is meant the force required to break a given material. Thus, by providing a reinforcement layer having an ultimate tensile strength being greater than an ultimate tensile strength of the top film and/or the one or more electrodes, it ensured that an external load (such as a user handling the base plate) does not accidentally rupture the electrodes of the electrode assembly provided on the top film. Rather, by carrying the load, the reinforcement layer will prevent the one or more electrodes from rupturing.

In an embodiment, a thickness of the reinforcement layer is greater than a thickness of the top film. Thereby, the elastic properties of the reinforcement layer can be manipulated by providing a certain thickness rather than choosing a different material. In embodiments, the thickness of the reinforcement layer varies, such that its ability to carry a load varies across the base plate.

In embodiments, the top film as such has an elongation at break between 500% and 600%, such as between 510% and 560%, such as between 540% and 560%. Here, the elongation at break of the top film relates to the top film when isolated from other parts. Thus, the elongation at break as stated here is true for a top film prior to arranging the top film in a base plate for an ostomy appliance. Thus, it is noted that additional parts, such as the first adhesive layer or a reinforcement layer as introduced below, and a bonding therebetween, may reduce the elongation of the top film. Providing a top film having an elongation at break between 500% and 600%, when isolated, provides for a very elastic and flexible base plate. However, the elongation at break of between 500% and 600% increases the risk of rupturing the electrodes of the electrode assembly, which are considerably less stretchable due to its conductive properties and the printing method. Thus, by introducing a reinforcement layer having suitable figures in terms of tensile strength reduces the stress on the electrodes and thus inhibits such rupturing/overstretching.

In embodiments, the reinforcement layer is arranged on the proximal surface of the top film, such as covering at least parts of the electrode assembly and thus the one or more electrodes thereof. In embodiments, the reinforcement layer is arranged on the distal surface of the first adhesive layer. In embodiments, the reinforcement layer is arranged on the distal surface of the top film, and thus of the base plate.

In an embodiment, the reinforcement layer is arranged between the proximal surface of the top film and the distal surface of the first adhesive layer. For example, the reinforcement layer may be applied to the proximal surface of the top film after electrodes of the electrode assembly have been arranged thereupon. Thereby, the reinforcement layer may cover at least parts of the electrode assembly, such that, in regions of the base plate, the reinforcement layer is sandwiched between the electrode assembly and the distal surface of the first adhesive layer, and in other regions of the base plate, the reinforcement layer is sandwiched between the proximal surface of the top film and the distal surface of the first adhesive layer.

In embodiments, the reinforcement layer is arranged in a predefined pattern on the proximal surface of the top film and/or electrode assembly. Thus, in an embodiment, the reinforcement layer covers at least parts of the electrode assembly. In embodiments, at least parts of the electrode assembly are sandwiched between the proximal surface of the top film and the reinforcement layer. Thereby, the elasticity of the covered parts of the electrode assembly is reduced to the elasticity of the reinforcement layer. In other words, by covering at least parts of the one or more electrodes of the electrode assembly, the reinforcement layer is capable of carrying an external load (e.g., user handling), thereby protecting the electrodes. In embodiments, the reinforcement layer exposes portions of the electrode assembly, such that said portions of the electrode assembly are in direct contact with the first adhesive layer, thereby allowing for an electrical connection with the first adhesive layer, such as for allowing resistance measurements of the first adhesive layer. Thus, in embodiments, the reinforcement layer exposes at least portions of the electrode assembly, such as to the first adhesive layer.

In an embodiment, the reinforcement layer is electrically insulating. Thereby, the reinforcement layer can insulate portions of the electrode assembly from the first adhesive layer, such as to define a series of sensing parts along the one or more electrodes of the electrode assembly where resistance measurements can be made, whereas other regions of the electrode assembly can be masked/insulated from the first adhesive layer, such as to avoid measuring the resistance of the first adhesive layer in these masked regions.

In an embodiment, the reinforcement layer is a lacquer. For example, the lacquer can be deposited in a predefined pattern on the proximal surface of the top film and electrode assembly arranged thereupon and subsequently cured/hardened to achieve the properties of the reinforcement layer as disclosed herein. Afterwards, the combined top film, electrode assembly, and reinforcement layer can be arranged adjacent to the distal surface of a first adhesive layer. Thereby is provided a way of arranging a reinforcement layer on the top film. In an embodiment, the lacquer is an acrylate lacquer, such as a UV curable acrylate lacquer. In alternative embodiments, other types of lacquers may be used, such as chemically curable lacquers and/or heat curable lacquers.

In a second aspect of the invention, a method for manufacturing a base plate for an ostomy appliance is disclosed. The base plate has a proximal surface and a distal surface. The method comprises the steps of printing an electrode assembly on a proximal surface of a top film having the proximal surface and a distal surface, the electrode assembly comprising one or more electrodes, providing a first adhesive layer having a proximal surface and a distal surface, and arranging the proximal surface of the top film adjacent to the distal surface of the first adhesive layer such that the distal surface of the top film forms/is the distal surface of the base plate.

Thus, the method according to the second aspect of the invention provides a method for manufacturing the base plate as discussed in relation to the first aspect of the invention. Embodiments and alternatives discussed in relation to the first aspect of the invention are considered applicable. In examples, the method is a method for manufacturing a sensor patch, such as the sensor patch discussed in relation to examples of the first aspect of the invention.

The method provides a simple and cost-efficient way of manufacturing a base plate having sensing means through the provision of an electrode assembly. In particular, the method is considered cost-efficient due to the top film being the only film included in the base plate; the top film is both the protective film for the distal surface of the first adhesive layer and the support for the electrode assembly.

In embodiments, the step of printing an electrode assembly on a proximal surface of a top film may be substituted by the step of arranging an electrode assembly on a proximal surface of a top film.

In an embodiment, the step of arranging the proximal surface of the top film adjacent to the distal surface of the first adhesive layer includes arranging the proximal surface of the top film on the distal surface of the first adhesive layer. Here, it is understood that the electrode assembly on the proximal surface of the top film becomes sandwiched between the first adhesive layer and the top film. Thereby is provided that the top film is the only film covering the entire surface of the distal side of the base plate, namely because the top film is also the distal surface of the base plate as such.

In an embodiment, printing an electrode assembly includes printing one or more conductive traces on the proximal surface of the top film. By conductive traces is meant electrically conductive paths formed from a printing process using conductive ink. Thus, the conductive traces form the one or more electrodes of the electrode assembly. Printing is considered a cost- and waste-efficient way of providing electrodes on a flexible substrate, such as the top film according to the first and second aspects of the invention. The conductive ink may comprise graphite/carbon, silver, or other electrically conductive materials suitable for a printing process.

In an embodiment, the method comprises the intermediate step of arranging a reinforcement layer according to a predefined pattern on a surface of the top film, the reinforcement layer inhibiting overstretching of the one or more electrodes of the electrode assembly. For example, the reinforcement layer is arranged according to a predefined pattern on the proximal surface of the top film/electrode assembly. For example, the reinforcement layer can be arranged such that it covers at least parts of the electrode assembly. In embodiments, the reinforcement layer is bonded to the top film and/or electrode assembly, such that the reinforcement layer can carry a load exerted on the base plate.

In an embodiment, arranging a reinforcement layer comprises depositing a lacquer according to the predefined pattern. In embodiments, the lacquer is subsequently cured, such as by means of UV-light, a chemical process, or heat. In embodiments, the lacquer is a UV-curable acrylate lacquer. Thereby is provided means for an efficient method for arranging a reinforcement layer on the top film. Further, by depositing the reinforcement layer is provided a versatile method allowing for quickly adapting or amending the predefined pattern, e.g., between batches of base plates, or according to desired needs in different products incorporating the reinforcement layer.

In embodiments, the depositing method and the choice of lacquer provides for the reinforcement layer being immediately bonded to the top film, e.g., through a curing process.

DETAILED DESCRIPTION OF THE DRAWINGS

FIG. 1 illustrates an exploded view of a base plate 10 according to an embodiment of the invention. The base plate 10 comprises a first adhesive layer 110, a reinforcement layer 140, an electrode assembly 120, and a top film 100. In alternative embodiments of the invention, the reinforcement layer 140 is omitted, whereby the base plate 10 comprises the first adhesive layer 110, the electrode assembly 120, and the top film 100.

The first adhesive layer 110 comprises a proximal surface 111, a distal surface 112, and a stomal opening 113. The proximal surface 111 of the first adhesive layer 110 is adapted for attachment to a skin surface of a user, e.g., after removal of a protective release liner (not shown). Thus, proximal surface 111 of the first adhesive layer 110 may double as the proximal surface 11 of the assembled base plate 10. The top film 100 comprises a proximal surface 101, a distal surface 102, and a stomal opening 103. The distal surface 102 of the top film 100 doubles as the distal surface 12 of the assembled base plate 10. The electrode assembly 120 comprises a plurality of electrodes 120' and a monitor interface 123 allowing for an electrical connection between the electrodes 120' and a monitor device couplable to the monitor interface. The reinforcement layer 140 is arranged on the proximal side/surface 101 of the top film 100, such that the reinforcement layer 140 covers at least parts of the electrode assembly 120, whereby said parts of the electrode assembly are sandwiched between the reinforcement layer 140 and the top film 100. Thereby, the reinforcement layer 140 may inhibit overstretching of the electrodes 120' as previously discussed. Further, the illustrated reinforcement layer 140 comprises a plurality of openings 141 exposing sensing parts of the electrodes 120', in particular exposing said sensing parts to the distal surface 112 of the first adhesive layer 110. In embodiments where the reinforcement layer 140 is electrically insulating, the plurality of openings 141 allows for manipulating how and where electrical measurements of the first adhesive layer 110 are made by means of the electrodes 120' and a monitor device coupled to the electrode assembly 120.

Figure 2:
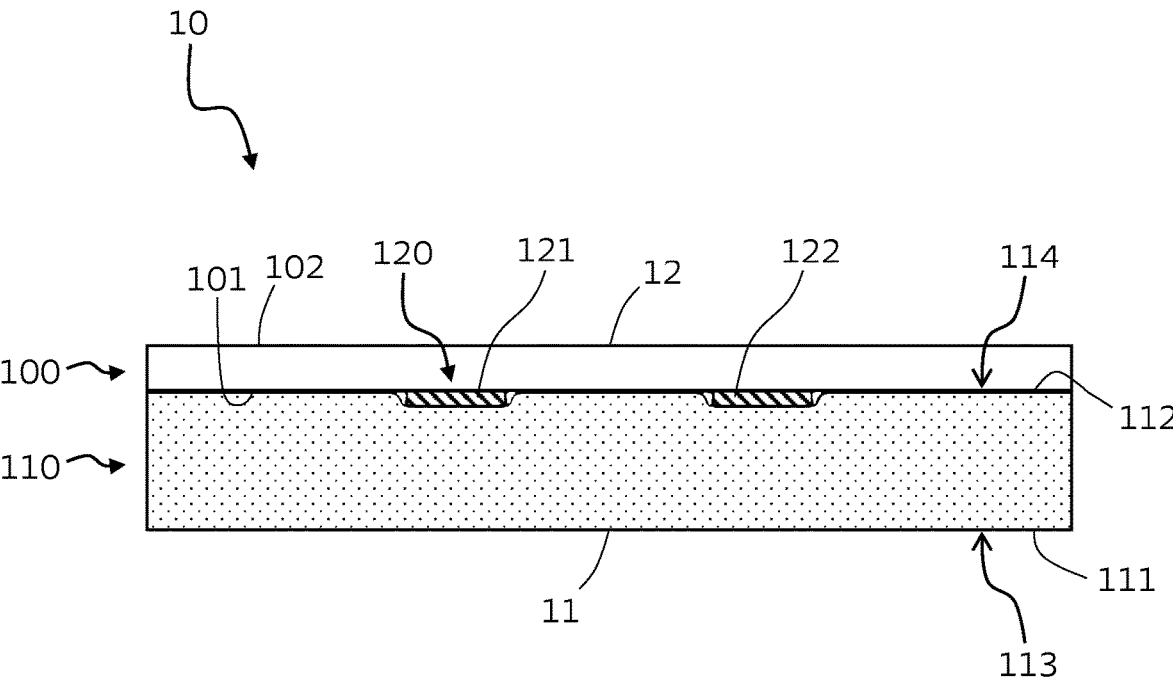
FIG. 2 illustrates a cross-sectional view of a part of a base plate according to an embodiment of the invention.

FIG. 2 illustrates a cross-sectional view of a part of a base plate 10 according to an embodiment of the invention. The illustrated base plate 10 comprises a first adhesive layer 110, an electrode assembly 120, and a top film 100. The electrode assembly 120 is illustrated as two separate electrodes 121, 122, but the electrode assembly may comprise less or more electrodes. None of the illustrated elements are necessarily drawn to scale. In particular, the crevasse in the first adhesive layer 110 formed by the electrodes 121, 122 is highly exaggerated and does not necessarily reflect reality where the thickness of the electrodes 121, 122 merely causes any deformation of neither the top film 100 nor the first adhesive layer 110.

The base plate 10 has a proximal surface 11 and a distal surface 12. The first adhesive layer 110 has a proximal side 113, including a proximal surface 111, and a distal side 114, including a distal surface 112. The top film 100 has a proximal surface 111 and a distal surface 112. The electrodes 121, 122, of the electrode assembly 120 are arranged, such as printed, on the proximal surface 101 of the top film 100.

The first adhesive layer 110 comprises a skin-friendly adhesive, such that the proximal surface 111 of the first adhesive layer 110 can be adhered to the skin surface of a user. According to embodiments, the first adhesive layer 110 has a thickness in the range from 0.1 mm to 1.5 mm, e.g., in the range from 0.2 mm to 1.2 mm, such as 0.8 mm or 1.0 mm.

The electrode assembly 120 comprises, according to the illustrated embodiment, two electrodes 121, 122. The two electrodes 121, 122 may be conductive traces formed by printing a conductive ink, such as silver or carbon, onto the proximal surface 101 of the top film 100. Thus, in embodiments, the electrode assembly 120 is provided on the proximal surface 101 of the top film 100 by means of a printing process. Thereby, the top film 100 and the electrode assembly 120 can be manufactured separately. Thus, the base plate 10 can be manufactured by arranging the combined top film 100 and electrode assembly 120 on the distal side 114 of the first adhesive layer 110.

The top film 110 is a flexible and elastic film, such as a flexible and elastic polymeric film. According to embodiments, the top film 110 is a (thermoplastic) polyurethane film.

According to the invention, the distal surface 102 of the top film 100 is the distal surface 12 of the base plate 10. Thus, the top film 100 is the most distal part of the base plate 10, and, at the same time, is the support for the electrode assembly arranged, e.g., printed, on the proximal surface 101 of the top film 100. Thus, the distal surface 102 of the top film 100 is the distal surface 12 of the base plate 10, whereas the proximal surface 101 of the top film 100 is support for the electrode assembly 120.

In the illustrated embodiment of FIG. 2, the electrode assembly 120 is in direct contact with the distal surface 112 of the first adhesive layer 110. Thereby, electricity can be conducted through the first adhesive layer 110 from a first electrode 121 to the second electrode 122 when a voltage is applied, e.g., by means of a monitor device coupled to the electrode assembly 120. Electrical quantities such as resistance, conductance, capacitance, and inductance of the first adhesive layer 110 may thus be derived. The electrical quantities may reveal certain information about the adhesive performance or "health" of the first adhesive layer 120. The electrode assembly 120 is protected from the environment by being layered between the (protective) top film 100 and the first adhesive layer 110. A voltage may be applied the electrodes 121, 122 by means of a monitor device comprising a battery and a processor and being mechanically and/or electrically attachable to the electrode assembly, e.g., through a monitor interface provided in the base plate (not shown).

The illustrated base plates of FIGS. 1 and 2 provide a base plate having one, and only one, film—namely the top film 100.

Figure 3:
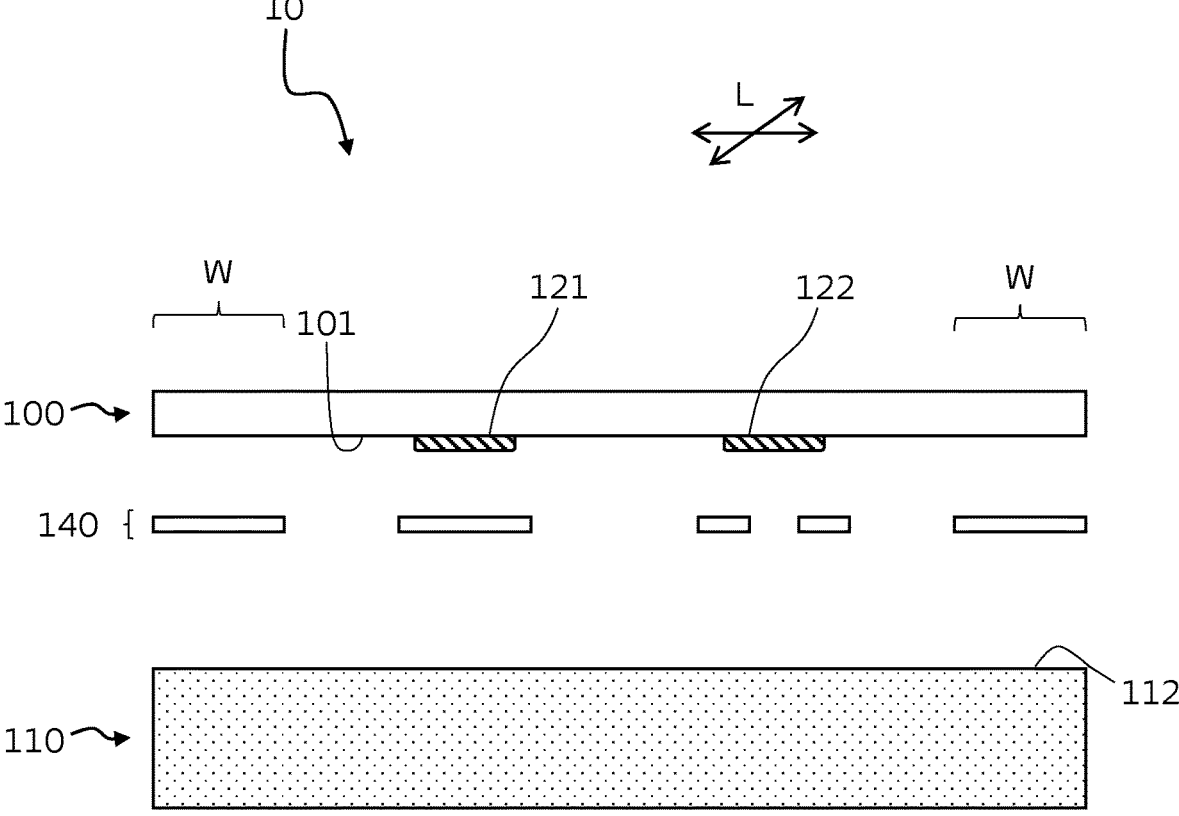
FIG. 3 illustrates an exploded cross-sectional view of a base plate according to an embodiment of the invention.

FIG. 3 illustrates an exploded cross-sectional view of a base plate 10 according to an embodiment of the invention. The embodiment of FIG. 3 illustrates the features of FIG. 2, as well as a reinforcement layer 140 arranged between the proximal surface 101 of the top film 100 and the distal surface 112 of the first adhesive layer 110. The reinforcement layer 140 is bonded to the proximal surface 101 of the top film 100 in an assembled embodiment, whereby the reinforcement layer 140 is able to carry a load applied to the top film 100 and/or base plate as such. In particular, the reinforcement layer 140 is able to carry a load in the directions indicated by the arrow L (thus, the directions being parallel to the extent of the base plate, also denoted the appliance plane). The reinforcement layer 140 inhibits over-stretching of the electrodes 121, 122 by carrying the load. The reinforcement layer 140 has a Young's modulus being greater than a Young's modulus of the top film 100, and/or the electrode assembly 120, and/or the first adhesive layer 110, whereby the reinforcement layer 140 limits the overall elasticity of the base plate 10 to a point where overstretching the electrodes 121, 122 is (greatly) reduced, such as inhib-ited.

The reinforcement layer 140 is arranged according to a predefined pattern designed according to the intended pur-pose of a given part of the base plate 10. In the illustrated embodiment of FIG. 3, the reinforcement layer 140 is arranged in edge portions W of the part of the base plate 10 illustrated. The edge portions W may be edge portions of the base plate, whereby the reinforcement layer reinforces the edges of the base plate. Further, the illustrated predefined pattern of the reinforcement layer 140 entirely covers the first electrode 121, such that said electrode is masked from the first adhesive layer 110 (i.e., at least in the given cross-sectional view). Where the reinforcement layer 140 is electrically insulating, such masking facilitates manipulat-ing how and/or where electrical quantities of the first adhe-sive layer 110 is measured. Further, the illustrated predefined pattern of the reinforcement layer 140 exposes the second electrode 122 to the first adhesive layer 110, such that said electrode 122 is in electrical contact with the first adhesive layer 110. The reinforcement layer 140 covers a part of the second electrode 122, such as to reinforce the electrode to inhibit overstretching, but without masking the electrode entirely from the first adhesive layer 110. Multiple different predefined patterns of the reinforcement layer 140 is fore-seen within the scope of the invention, and the illustrated embodiment comprising a certain predefined pattern of the reinforcement layer 140 is intended to merely highlight properties of the reinforcement layer 140.

Figure 4:
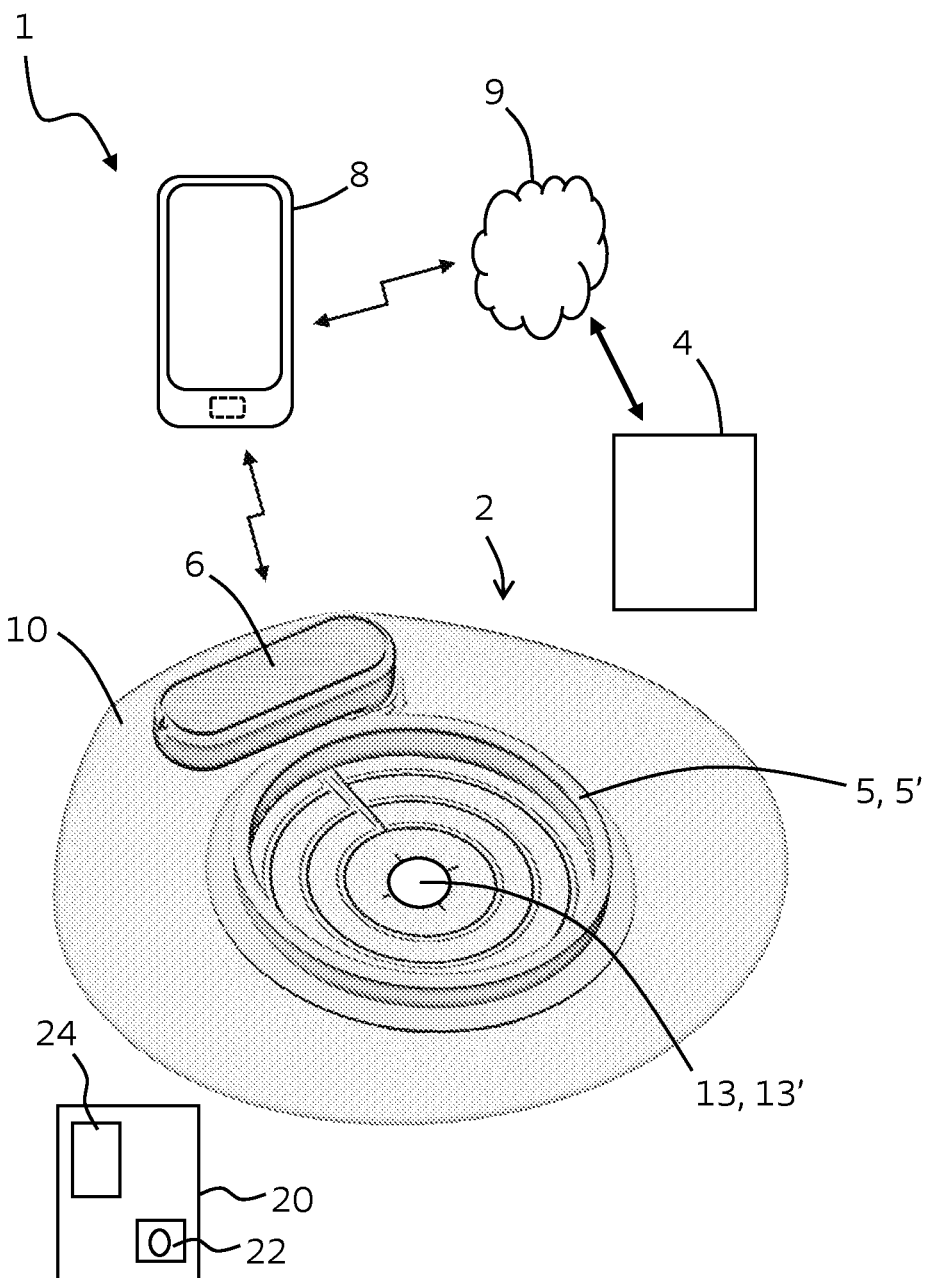
FIG. 4 illustrates an exemplary ostomy system.

FIG. 4 illustrates an exemplary ostomy system. The ostomy system 1 comprises an ostomy appliance 2 including a base plate 10 according to the invention. The base plate 10 is adapted to support an ostomy pouch (not shown). Further, the ostomy system 1 comprises a monitor device 6 and an accessory device 8 (mobile telephone). The monitor device 6 is connectable to the base plate 10 via respective first connectors of the monitor device 6 and base plate 10. The monitor device 6 is configured for wireless communication with the accessory device 8. Optionally, the accessory device 8 is configured to communicate with a server device 4 of the ostomy system 1, e.g., via network 9. The server device 4 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 10 comprises a coupling member 5 in the form of a coupling ring 5' for coupling an ostomy pouch (not shown) to the base plate (two-part ostomy appliance). The base plate 10 has a stomal opening 13 with a centre point 13'. The size and/or shape of the stomal opening 13 is typically adjusted by the user or nurse before application of the ostomy appliance to accom-modate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wire-lessly connecting the monitor device to the docking station. The docking station 20 comprises a user interface 24 for receiving user input and/or providing feedback to the user on the operational state of the docking station 20. The user interface 24 may comprise a touchscreen. The user interface 24 may comprise one or more physical buttons and/or one or more visual indicators, such as light emitting diodes.

Figure 5:
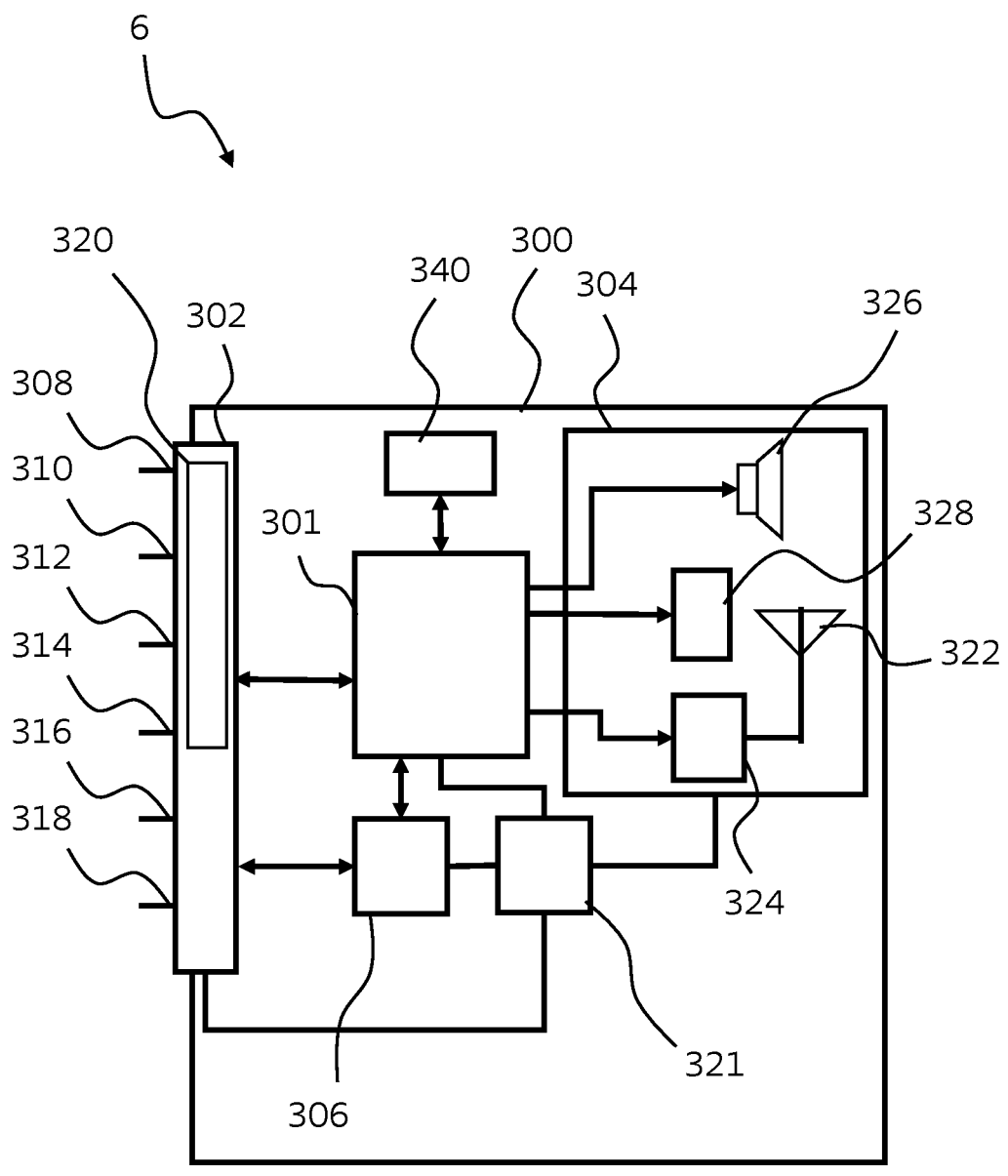
FIG. 5 illustrates a schematic block diagram of an exemplary monitor device.

FIG. 5 is a schematic block diagram of an exemplary monitor device 6. The monitor device 6 comprises a monitor device housing 300, a processor 301, and one or more interfaces, the one or more interfaces including a first interface 302 (appliance interface) and a second interface 304 (accessory interface). The monitor device 6 comprises a memory 306 for storing ostomy data and/or parameter data based on the ostomy data. The memory 306 is connected to the processor 301 and/or the first interface 302.

The first interface 302 is configured as an appliance interface for electrically and/or mechanically connecting the monitor device 6 to the ostomy appliance, e.g., ostomy appliance 2 of FIG. 4. The first interface 302 comprises a plurality of terminals for forming electrical connections with respective terminals of the ostomy appliance 2 (base plate 10, such as monitor interface 123 of FIG. 1). The first interface 302 comprises a ground terminal 308, a first terminal 310, a second terminal 312 and a third terminal 314. The first interface 302 optionally comprises a fourth termi-nal 316 and a fifth terminal 318. The first interface 302 of the monitor device 6 comprises a coupling part 320 for forming a mechanical connection, such as a releasable coupling between the monitor device and the base plate. The coupling part 320 and the terminals 308, 310, 312, 314, 316, and 318 of the first interface 302 form (at least part of) a first connector of the monitor device 6.

The monitor device 6 comprises a power unit 321 for powering the monitor device and active components thereof, i.e., the power unit 321 is connected to the processor 301, the first interface 302, the second interface 304, and memory 306. The power unit comprises a battery and charging circuitry. The charging circuitry is connected to the battery and terminals of the first interface 302 for charging the battery via terminals of the first interface, e.g., terminals of the first connector.

The second interface 304 of the monitor device is con-figured as an accessory interface for connecting the monitor device 6 to one or more accessory devices such as accessory device 8 of FIG. 4. The second interface 304 comprises an antenna 322 and a wireless transceiver 324 configured for wireless communication with accessory device(s). Option-ally, the second interface 304 comprises a loudspeaker 326 and/or a haptic feedback element 328 for provision of respective audio signal and/or haptic feedback to the user.

The monitor device 6 optionally comprises a sensor unit 340 connected to the processor 301. For example, the sensor unit 340 comprises a temperature sensor for feeding temperature data to the processor and/or a G-sensor or accelerometer for feeding acceleration data to the processor 301. Additionally and/or alternatively, the sensor unit 340 comprises a humidity sensor and/or an acoustic sensor. The sensor unit 340 may comprise alternative and/or additional sensors suitable and/or relevant to an ostomy system as described.

The processor 301 is configured to apply a processing scheme, and the first interface 302 is configured for collecting ostomy data from the base plate and/or the sensor patch coupled to the first interface, the ostomy data comprising first ostomy data from a first electrode pair of the base plate and/or the sensor patch, second ostomy data from a second electrode pair of the base plate and/or the sensor patch, and third ostomy data from a third electrode pair of the base plate and/or the sensor patch. The ostomy data may be stored in the memory 306 and/or processed in the processor 301 in order to obtain parameter data. The parameter data may be stored in the memory 306. The processor 301 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 301 is configured to obtain first, second and third parameter data based on respective first, second and third ostomy data. To apply a processing scheme comprises to determine an operating state of the base plate and/or the sensor assembly part of the ostomy appliance based on one or more, e.g., all, of the first parameter data, the second parameter data and the third parameter data, wherein the operating state is indicative of a degree of radial erosion of the base plate and/or the sensor assembly part and/or acute leakage risk for the ostomy appliance. The monitor device 6 is configured to, in accordance with a determination that the operating state is a first operating state, transmit a first monitor signal comprising monitor data indicative of the first operating state of the base plate and/or the sensor assembly part via the second interface; and in accordance with a determination that the operating state is a second operating state, transmit a second monitor signal comprising monitor data indicative of the second operating state of the base plate and/or the sensor assembly part via the second interface.

Whereas a base plate has been described with reference to the accompanying figures, it will be understood that similar descriptions and figures may apply to a sensor patch for attachment to the adhesive surface of a base plate, such as a generic base plate. Accordingly, the sensor patch may comprise the first adhesive layer, reinforcement layer, electrode assembly and top film as disclosed in embodiments herein.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly, to be regarded in an illustrative rather than restrictive sense. The claimed invention is intended to cover all alternatives, modifications, and equivalents.

Embodiments of the present disclosure are set out in the following items:

1. A sensor patch for attachment to a base plate of an ostomy appliance, the sensor patch having a proximal surface and a distal surface and comprising:

a first adhesive layer having a proximal side including a proximal surface and a distal side including a distal surface,
   an electrode assembly comprising one or more electrodes, and
   a top film having a proximal surface and a distal surface, the top film being arranged on the distal side of the first adhesive layer,
   wherein the electrode assembly is arranged on the proximal surface of the top film and wherein the distal surface of the top film is the distal surface of the sensor patch.

2. The sensor patch according to item 1, wherein the one or more electrodes of the electrode assembly are conductive traces.

3. The sensor patch according to any one of items 1 and 2, wherein at least parts of the electrode assembly are in contact with the distal surface of the first adhesive layer.

4. The sensor patch according to any one of items 1-3, wherein the proximal surface of the top film is in contact with the distal surface of the first adhesive layer.

5. The sensor patch according to any one of items 1-4, wherein the top film is made of a polymeric material.

6. The sensor patch according to any one of items 5, wherein the top film is the only polymeric film of the sensor patch.

7. The sensor patch according to any one of items 1-6, wherein the sensor patch further comprises a flexible reinforcement layer arranged on the distal side of the first adhesive layer.

8. The sensor patch according to item 7, wherein the reinforcement layer is bonded to the top film.

9. The sensor patch according to any one of items 7 and 8, wherein the reinforcement layer is arranged between the proximal surface of the top film and the distal surface of the first adhesive layer.

10. The sensor patch according to any one of items 7-9, wherein the reinforcement layer covers at least parts of the electrode assembly.

11. The sensor patch according to any one of items 7-10, wherein the reinforcement layer has a Young's modulus being greater than a Young's modulus of the top film.

12. The sensor patch according to any one of items 7-11, wherein a thickness of the reinforcement layer is greater than a thickness of the top film.

13. The sensor patch according to any one of items 7-12, wherein the reinforcement layer inhibits overstretching the one or more electrodes of the electrode assembly.

14. The sensor patch according to any one of items 7-13, wherein the reinforcement layer is electrically insulating.

15. The sensor patch according to any one of items 7-14, wherein the reinforcement layer is a lacquer.

16. The sensor patch according to item 15, wherein the lacquer is an acrylate lacquer.

17. A method for manufacturing a sensor patch for attachment to a base plate of an ostomy appliance, the sensor patch having a proximal surface and a distal surface, the method comprising the steps of
    printing an electrode assembly on a proximal surface of a top film having the proximal surface and a distal surface, the electrode assembly comprising one or more electrodes,
    providing a first adhesive layer having a proximal surface and a distal surface, and arranging the proximal surface of the top film adjacent to the distal surface of the first adhesive layer such that the distal surface of the top film forms the distal surface of the sensor patch.

18. The method according to item 17, wherein arranging the proximal surface of the top film adjacent to the distal surface of the first adhesive layer includes arranging the proximal surface of the top film on the distal surface of the first adhesive layer, whereby the electrode assembly becomes sandwiched between the first adhesive layer and the top film.

19. The method according to any one of items 17 and 18, wherein printing an electrode assembly includes printing one or more conductive traces on the proximal surface of the top film.

20. The method according to any one of items 17-19, wherein the method comprises the intermediate step of arranging a reinforcement layer according to a predefined pattern on a surface of the top film, the reinforcement layer inhibiting overstretching of the one or more electrodes of the electrode assembly.

21. The method according to item 20, wherein arranging a reinforcement layer comprises depositing a lacquer according to the predefined pattern.

The invention claimed is:

1. A base plate for an ostomy appliance, the base plate comprising:
a first adhesive layer having a proximal side including a proximal surface and a distal side including a distal surface, wherein the proximal surface of the adhesive layer forms a proximal surface of the base plate,
an electrode assembly comprising one or more electrodes, and
a top film having a proximal surface and a distal surface, the top film being arranged on the distal side of the first adhesive layer, wherein;
the electrode assembly is arranged on the proximal surface of the top film and wherein the distal surface of the top film forms a distal surface of the base plate, and
the proximal surface of the top film is in contact with the distal surface of the first adhesive layer.

2. The base plate according to claim 1, wherein the one or more electrodes of the electrode assembly are conductive traces.

3. The base plate according to claim 1, wherein at least parts of the electrode assembly are in contact with the distal surface of the first adhesive layer.

4. The base plate according to claim 1, wherein the top film is made of a polymeric material.

5. The base plate according to claim 4, wherein the top film is the only polymeric film of the base plate.

6. The base plate according to claim 1, wherein the base plate further comprises a flexible reinforcement layer arranged on the distal side of the first adhesive layer.

7. The base plate according to claim 6, wherein the reinforcement layer is bonded to the top film.

8. The base plate according to claim 6, wherein the reinforcement layer is arranged between the proximal surface of the top film and the distal surface of the first adhesive layer.

9. The base plate according to claim 6, wherein the reinforcement layer covers at least parts of the electrode assembly.

10. The base plate according to claim 6, wherein the reinforcement layer has a Young's modulus being greater than a Young's modulus of the top film.

11. The base plate according to claim 6, wherein a thickness of the reinforcement layer is greater than a thickness of the top film.

12. The base plate according to claim 6, wherein the reinforcement layer inhibits overstretching the one or more electrodes of the electrode assembly.

13. The base plate according to claim 6, wherein the reinforcement layer is electrically insulating.

14. The base plate according to claim 6, wherein the reinforcement layer is a lacquer.

15. A method for manufacturing a base plate for an ostomy appliance, the method comprising:
printing an electrode assembly on a proximal surface of a top film having the proximal surface and a distal surface, the electrode assembly comprising one or more electrodes,
providing a first adhesive layer having a proximal surface and a distal surface, and
arranging the proximal surface of the top film adjacent to the distal surface of the first adhesive layer such that:
the proximal surface of the first adhesive layer forms a proximal surface of the base plate,
the distal surface of the top film forms a distal surface of the base plate, and
at least a part of the electrode assembly is directly between the proximal surface of the top film and the distal surface of the adhesive layer.

16. The method according to claim 15, wherein arranging the proximal surface of the top film adjacent to the distal surface of the first adhesive layer includes arranging the proximal surface of the top film on the distal surface of the first adhesive layer, whereby the electrode assembly becomes sandwiched between the first adhesive layer and the top film.

17. The method according to claim 15, wherein printing an electrode assembly includes printing one or more conductive traces on the proximal surface of the top film.

18. The method according to claim 15, wherein the method comprises the intermediate step of arranging a reinforcement layer according to a predefined pattern on the proximal surface of the top film, the reinforcement layer inhibiting overstretching of the one or more electrodes of the electrode assembly.

19. The method according to claim 18, wherein arranging a reinforcement layer comprises depositing a lacquer according to the predefined pattern.

20. The base plate according to claim 1, wherein the top film is both:
configured to both provide support for the electrode assembly, and
sized to act as a protective film for the distal side of the base plate.

21. A base plate for an ostomy appliance, the base plate comprising:
an adhesive layer, comprising a proximal side configured for attachment to a skin surface of a user and a distal side including a distal surface;
a top film comprising a proximal surface and a distal surface, the distal surface of the top film forming a distal surface of the base plate; and
an electrode assembly between the distal surface of the adhesive layer and the proximal surface of the top film, wherein:
at least a part of the electrode assembly is in contact with both the distal surface of the adhesive layer and the proximal surface of the top film, and at least a part of the distal surface of the adhesive layer is in contact with the proximal surface of the top film.

\* \* \* \* \*